(12) United States Patent
Nakata

(10) Patent No.: US 7,834,325 B2
(45) Date of Patent: Nov. 16, 2010

(54) RADIATION IMAGE INFORMATION CAPTURING APPARATUS AND METHOD OF DETECTING TEMPERATURE OF AMPLIFIER THEREOF

(75) Inventor: Hajime Nakata, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 189 days.

(21) Appl. No.: 11/723,619

(22) Filed: Mar. 21, 2007

(65) Prior Publication Data

US 2007/0221859 A1   Sep. 27, 2007

(30) Foreign Application Priority Data

Mar. 24, 2006   (JP)   ............... 2006-081989
Mar. 28, 2006   (JP)   ............... 2006-088121

(51) Int. Cl.
*G01T 1/24*   (2006.01)
*H01L 23/34*   (2006.01)

(52) U.S. Cl. ............... 250/370.15; 250/370.09; 378/51

(58) Field of Classification Search ............ 250/370.09, 250/370.11, 370.015; 378/51
See application file for complete search history.

(56) References Cited

U.S. PATENT DOCUMENTS

| | | | | |
|---|---|---|---|---|
| 6,265,720 B1 * | 7/2001 | Yamazaki et al. | ...... | 250/370.09 |
| 6,323,891 B1 * | 11/2001 | Kitani et al. | ...... | 347/263 |
| 6,407,390 B1 * | 6/2002 | Rozsa | ...... | 250/363.01 |
| 6,653,637 B2 * | 11/2003 | Ochiai et al. | ...... | 250/397 |
| 2005/0067579 A1 * | 3/2005 | Tsuchiya et al. | ...... | 250/370.15 |
| 2006/0054829 A1 * | 3/2006 | Tsuchino et al. | ...... | 250/370.09 |
| 2006/0065848 A1 * | 3/2006 | Ueno et al. | ...... | 250/370.15 |
| 2009/0084971 A1 * | 4/2009 | Ohta et al. | ...... | 250/370.15 |

FOREIGN PATENT DOCUMENTS

| | | | |
|---|---|---|---|
| JP | 2000-37374 A | | 2/2000 |
| JP | 2000-116633 A | | 4/2000 |
| JP | 2002-22841 A | | 1/2002 |
| JP | 2002022841 A | * | 1/2002 |
| JP | 2004-154409 A | | 6/2004 |

* cited by examiner

*Primary Examiner*—David P Porta
*Assistant Examiner*—Casey Bryant
(74) *Attorney, Agent, or Firm*—Sughrue Mion, PLLC

(57) ABSTRACT

Amplifiers are mounted on flexible boards connected to a solid-state detector. A first temperature adjustment member is disposed near one of the surfaces of the amplifiers and the flexible boards, and a second temperature adjustment member is disposed near the other surface of the flexible boards. The first temperature adjustment member adjusts the temperature of the amplifiers themselves, and prevents heat from being transferred from the one of the surfaces of the flexible boards to the solid-state detector. The second temperature adjustment member prevents heat from being transferred from the other surface of the flexible boards to the solid-state detector.

16 Claims, 14 Drawing Sheets

RADIATION IMAGE INFORMATION CAPTURING APPARATUS AND METHOD OF DETECTING TEMPERATURE OF AMPLIFIER THEREOF

BACKGROUND OF THE INVENTION

1. Field of the Invention

The present invention relates to a radiation image information capturing apparatus for reading the radiation image information of a subject by converting the radiation image information into an electric signal, and a method of detecting the temperature of an amplifier of the radiation image information capturing apparatus.

2. Description of the Related Art

X-ray breast image capturing apparatus (mammographic apparatus) apply an X-ray radiation to a subject, i.e., a breast, to capture and record the radiation image of the subject in a radiation image recorder (solid-state detector), and read the recorded radiation image from the radiation image recorder by applying reading light from a reading light source to the radiation image recorder while moving the reading light source relatively to the radiation image recorder with a scanner to scan the radiation image recorder for thereby causing the radiation image recorder to emit light representing information depending on the recorded radiation image.

The radiation image recorder comprises a radiation solid-state detector made up of a matrix of photoelectric transducers and thin-film transistors (TFTs), and may be of the light reading type, the light conversion type, or the direction conversion type.

The radiation solid-state detector outputs an image signal in the form of an analog electric signal which represents a recorded radiation image. Since the output analog electric signal has a weak signal level, it is amplified by an amplifier.

The weak analog electric signal tends to be easily affected by temperature changes of the radiation solid-state detector and the amplifier. It is desirable to acquire radiation image information which is stable against temperature changes from the weak analog electric signal.

There is known a radiation image capturing apparatus disclosed in Japanese Laid-Open Patent Publication No. 2002-22841 (hereinafter referred to as "conventional art 1") for acquiring an image signal that is stable against temperature changes of an amplifier. As shown in FIG. 13 of the accompanying drawings, the known radiation image capturing apparatus has a sensor substrate 1 having a matrix of pixels including photoelectric transducers and TFTs (converting means). The sensor substrate 1 is made of glass, and a fluorescent layer 2 is disposed on the sensor substrate 1.

A detecting integrated circuit IC (amplifying means) is mounted on a surface of a flexible board 3 having an end electrically connected to the sensor substrate 1 and another end electrically connected to a signal processing circuit substrate 4. A cooling fin unit 5 for radiating the heat generated by the detecting integrated circuit IC is held in contact with a heat transmitter 6 mounted on the detecting integrated circuit IC. The cooling fin unit 5 is coupled by sleeves 9 to an elastic plate 7 and a fixing plate 8 which are mounted on the opposite surface of the flexible board 3 that is remote from the detecting integrated circuit IC.

According to the conventional art 1, the cooling fin unit 5 is positioned only on the side of the surface of the flexible board 3 on which the detecting integrated circuit IC is mounted. Therefore, the heat generated by the detecting integrated circuit IC tends to flow to the sensor substrate 1 along the opposite surface of the flexible board 3 that is remote from the detecting integrated circuit IC.

Japanese Laid-Open Patent Publication No. 2000-116633 (hereinafter referred to as "conventional art 2") discloses another radiation image capturing apparatus having a sensor substrate surrounded by a flexible circuit board. Upper and lower shield members are mounted respectively on upper and lower surfaces of the flexible circuit board with upper and lower heat insulators interposed therebetween. The lower shield member has a lower surface held against an inner frame, and the upper shield member has an upper surface held against an outer frame having a large volume.

According to the conventional art 2, the flexible circuit board is vertically sandwiched by the upper and lower shield members. Heat from an amplifying means is not prevented from being transferred through the flexible circuit board to the sensor substrate.

Japanese Laid-Open Patent Publication No. 2000-37374 (hereinafter referred to as "conventional art 3") discloses still another radiation image capturing apparatus. As shown in FIG. 14 of the accompanying drawings, the disclosed radiation image capturing apparatus has an image capturing device 2a vertically movably supported on a mount base 1a. The image capturing device 2a includes a two-dimensional radiation detector 3a and a signal converter 4a for converting a signal from the two-dimensional radiation detector 3a into an image signal. The two-dimensional radiation detector 3a and the signal converter 4a are arranged successively from an X-ray tube, not shown.

A fan 5a as a cooling means is mounted in an upper end of the image capturing device 2a. An external air inlet port 2b is defined in a lower end of the image capturing device 2a. The signal converter 4a is electrically connected by a cable 6a to an image processor 8a and a power supply 9a in a controller 7a.

The controller 7a, which accommodates the image processor 8a and the power supply 9a therein, is positioned outside of the image capturing device 2a. Therefore, the image capturing device 2a is small in size, and the two-dimensional radiation detector 3a is effectively cooled by the fan 5a.

According to the conventional art 3, however, since external air is directly introduced from the external air inlet port 2b into the image capturing device 2a by the fan 5a, the temperature of a coolant, i.e., air, in the image capturing device 2a depends on the ambient temperature around the image capturing device 2a. Consequently, the temperature of the coolant drawn into the image capturing device 2a tends to vary, and the temperature in the image capturing device 2a cannot be controlled to a nicety.

In addition, the power supply 9a, which includes a power supply unit for the signal converter 4a, is disposed outside of and spaced from the image capturing device 2a. As a result, the power transmission path along the cable 6a from the power supply 9a to the signal converter 4a is long enough to pick up external noise.

SUMMARY OF THE INVENTION

It is a general object of the present invention to provide a radiation image information capturing apparatus which is of a simple structure and capable of effectively controlling the temperature of an amplifier and reliably preventing heat from being transferred from the amplifier to a converter to efficiently obtain high-quality radiation image information, and a method of detecting the temperature of the amplifier.

A major object of the present invention is to provide a radiation image information capturing apparatus which is of a small size and capable of reliably controlling temperatures highly accurately without being affected by ambient temperatures to efficiently obtain high-quality radiation image information.

According to the present invention, there is provided a radiation image information capturing apparatus for reading the radiation image information of a subject by converting the radiation image information into an electric signal.

The radiation image information capturing apparatus has a converter for converting the radiation image information of the subject into the electric signal, an amplifier connected to the converter by a signal line for amplifying the electric signal produced by the converter, a first temperature adjustment member disposed near one surface of the amplifier and the signal line, and a second temperature adjustment member disposed near another surface of the signal line.

The first temperature adjustment member or the second temperature adjustment member may have a holder for holding the converter. The first temperature adjustment member or the second temperature adjustment member may comprise a Peltier device. Preferably, the radiation image information capturing apparatus further has a temperature detector for detecting the temperature of the amplifier.

The temperature detector may comprise a plurality of thermistors each of which is disposed on each side of the amplifier. The amplifier and the signal line may be controlled in a temperature range from 20° C. to 40° C. by the first temperature adjustment member and the second temperature adjustment member.

According to the present invention, there is also provided a method of detecting the temperature of an amplifier in a radiation image information capturing apparatus in which a converter for converting the radiation image information of a subject into an electric signal is connected by a signal line to the amplifier for amplifying the electric signal generated by the converter. The method comprises the steps of detecting temperatures respectively with first temperature detecting means disposed on one side of the amplifier and second temperature detecting means disposed on the other side of the amplifier, and setting $(\theta_j+\theta_{j+1})/2$ as the temperature of the amplifier where $\theta_j$ represents the temperature detected by the first temperature detecting means and $\theta_{j+1}$ represents the temperature detected by the second temperature detecting means.

According to the present invention, there is also provided a radiation image information capturing apparatus for reading the radiation image information of a subject by converting the radiation image information into an electric signal. The radiation image information capturing apparatus has a casing housing therein a converter for converting the radiation image information of the subject into the electric signal, an amplifier for amplifying the electric signal produced by the converter, a signal processor for processing the amplified electric signal, and a device power supply unit for supplying a power supply voltage at least to the converter, and a control power supply unit disposed outside the casing.

The casing has a space defined therein which is essentially closed from outside of the casing, and a heat exchanger is supported on the casing for adjusting the temperature of air in the space through a heat exchange with a heat medium outside the casing. The heat medium may be external air, an external coolant, an external heat transfer member, or the like.

The radiation image information capturing apparatus preferably further comprise a temperature measuring unit disposed in the casing for detecting the temperature in the space. The temperature in the space may be controlled in a temperature range from 20° C. to 40° C.

The heat exchanger may comprise a Peltier device. The heat exchanger may perform a heat exchange between air in the space and external air outside the casing. Alternatively, the heat exchanger may perform a heat exchange between air in the space and the casing.

The radiation image information capturing apparatus may further comprise a temperature adjuster disposed in the casing for adjusting the temperature of at least the amplifier. The radiation image information capturing apparatus may further comprise a heat insulating member disposed on an inner wall surface or an outer wall surface of the casing in enclosing relation to the space.

According to the present invention, the first temperature adjustment member adjusts the temperature of the amplifier itself and prevents heat from being transferred from the one surface of the signal line. The second temperature adjustment member prevents heat from being transferred from the other surface of the signal line. Accordingly, the temperature of the amplifier itself is effectively adjusted, and heat is prevented from being transferred from the amplifier to the converter through the signal line, with the simple structure. The converter is thus allowed to produce high-quality radiation image information efficiently.

The temperature of the amplifier is detected highly accurately and reliably based on the temperatures detected by the first temperature detecting means and the second temperature detecting means. Consequently, the temperature of the amplifier is controlled efficiently.

Furthermore, since the control power supply unit is disposed outside the casing, the casing is relatively small in overall size. Because the device power supply unit is housed in the casing, the power transmission path between the device power supply unit and the converter is so short that the power transmission path does not pick up unwanted external noise.

The essentially closed space is defined in the casing, and the air in the space is adjusted in temperature by the heat exchanger. Therefore, the temperature of the air in the space is not affected by the temperature of ambient air unlike the conventional system wherein external air is directly drawn into the casing. It is thus possible to control the temperature of the air in the casing easily and reliably with high accuracy for efficiently obtaining high-quality radiation image information.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
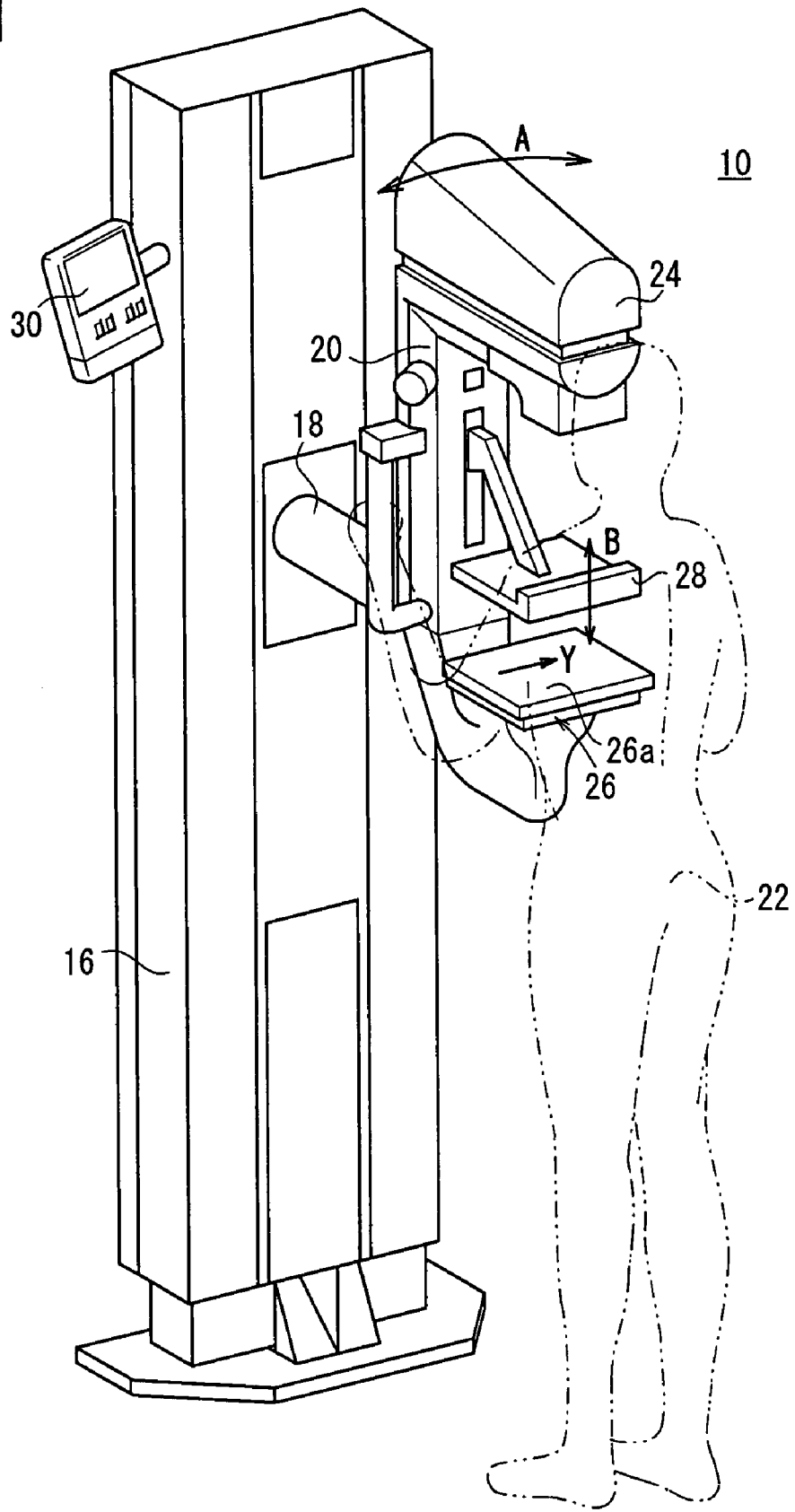
FIG. 1 is a perspective view of a mammographic apparatus according to a first embodiment of the present invention.

FIG. 1 shows in perspective a mammographic apparatus 10 which is a radiation image information capturing apparatus according to a first embodiment of the present invention.

As shown in FIG. 1, the mammographic apparatus 10 has an upstanding base 16, a vertical arm 20 fixed to a horizontal swing shaft 18 disposed substantially centrally on the base 16, a radiation source housing unit 24 fixed to an upper end of the arm 20 and housing a radiation source for applying a radiation to a subject 22, an image capturing base 26 fixed to a lower end of the arm 20, and a compression plate 28 for compressing and holding an image capturing region, i.e., a breast, of the subject 22 against the image capturing base 26. The image capturing base 26 houses a solid-state detector, to be described later, for detecting a radiation that has passed through the subject 22 to acquire radiation image information of the breast.

When the arm 20, to which the radiation source housing unit 24, the image capturing base 26, and the compression plate 28 are secured, is angularly moved about the swing shaft 18 in the directions indicated by the arrow A, an image capturing direction with respect to the image capturing region of the subject 22 is adjusted. The compression plate 28 is connected to the arm 20 and disposed between the radiation source housing unit 24 and the image capturing base 26. The compression plate 28 is vertically displaceable along the arm 20 in the directions indicated by the arrow B.

To the base 16, there is connected a display controller 30 for displaying image capturing information including an image capturing region, an image capturing direction, etc. of the subject 22 which have been detected by the mammographic apparatus 10 and the ID information of the subject 22, and setting these items of information when necessary.

Figure 2:
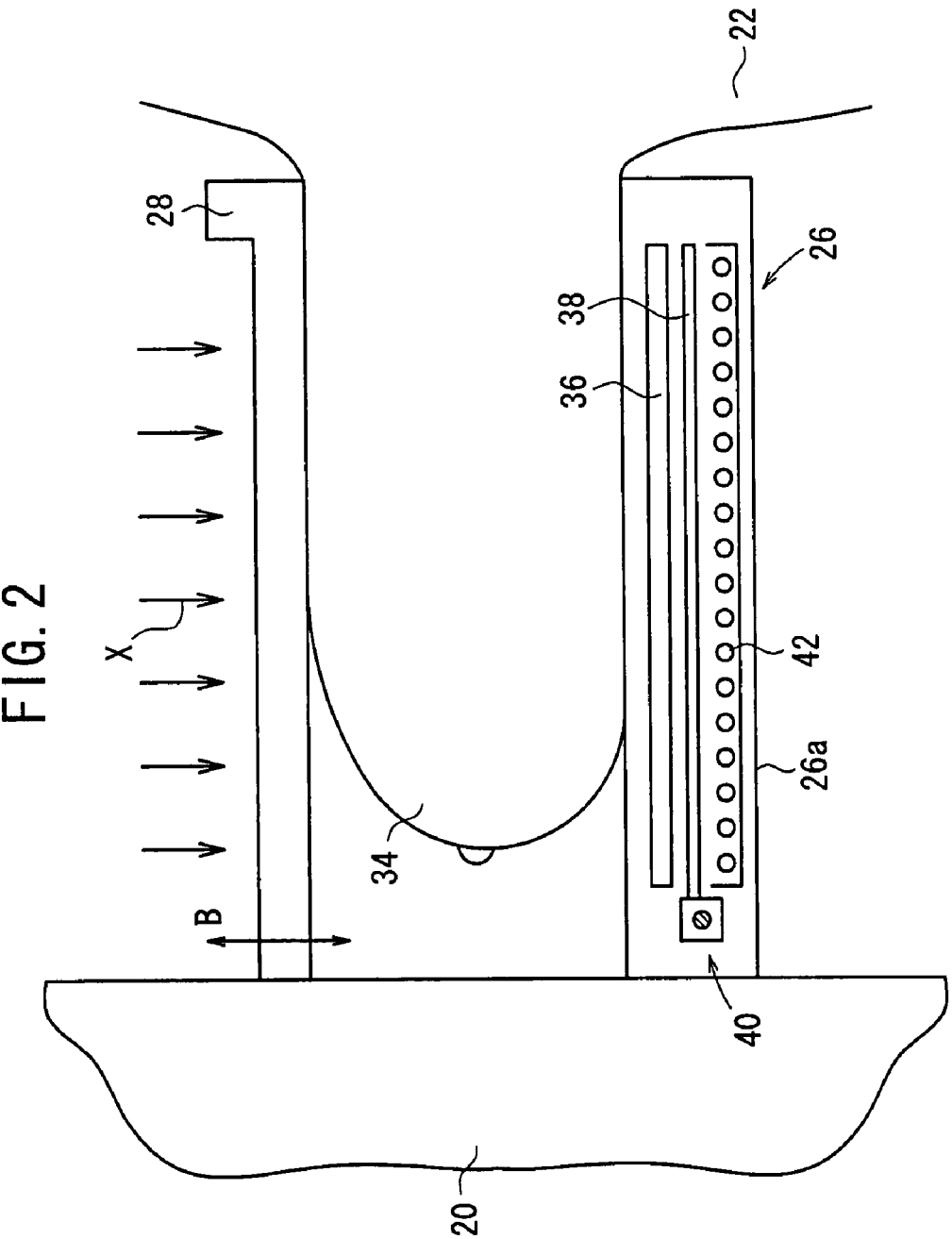
FIG. 2 is a fragmentary vertical elevational view, partly in cross section, showing internal structural details of an image capturing base of the mammographic apparatus shown in FIG. 1.

FIG. 2 shows internal structural details of the image capturing base 26. In FIG. 2, the image capturing region of the subject 22, i.e., a breast 34, is shown as being placed between the image capturing base 26 and the compression plate 28.

As shown in FIG. 2, the image capturing base 26 houses, in a casing 26a thereof, a solid-state detector (converter) 36 for storing radiation image information based on a radiation X emitted from the radiation source housed in the radiation source housing unit 24 and outputting an electric signal representative of the stored radiation image information, a reading light source 38 for applying reading light to the solid-state detector 36 to read radiation image information stored in the solid-state detector 36, a scanner 40 for moving the reading light source 38 in the direction indicated by the arrow Y (see FIG. 1) substantially parallel to a reading light scanning surface of the solid-state detector 36, and an erasing light source 42 for applying erasing light to the solid-state detector 36 to remove unwanted electric charges accumulated in the solid-state detector 36.

The solid-state detector 36 comprises a direct-conversion, light-reading radiation solid-state detector (converter). The solid-state detector 36 stores radiation image information represented by the radiation X that has passed through the breast 34 as an electrostatic latent image, and generates a current depending on the electrostatic latent image when the solid-state detector 36 is scanned by the reading light from the reading light source 38.

Figure 3:
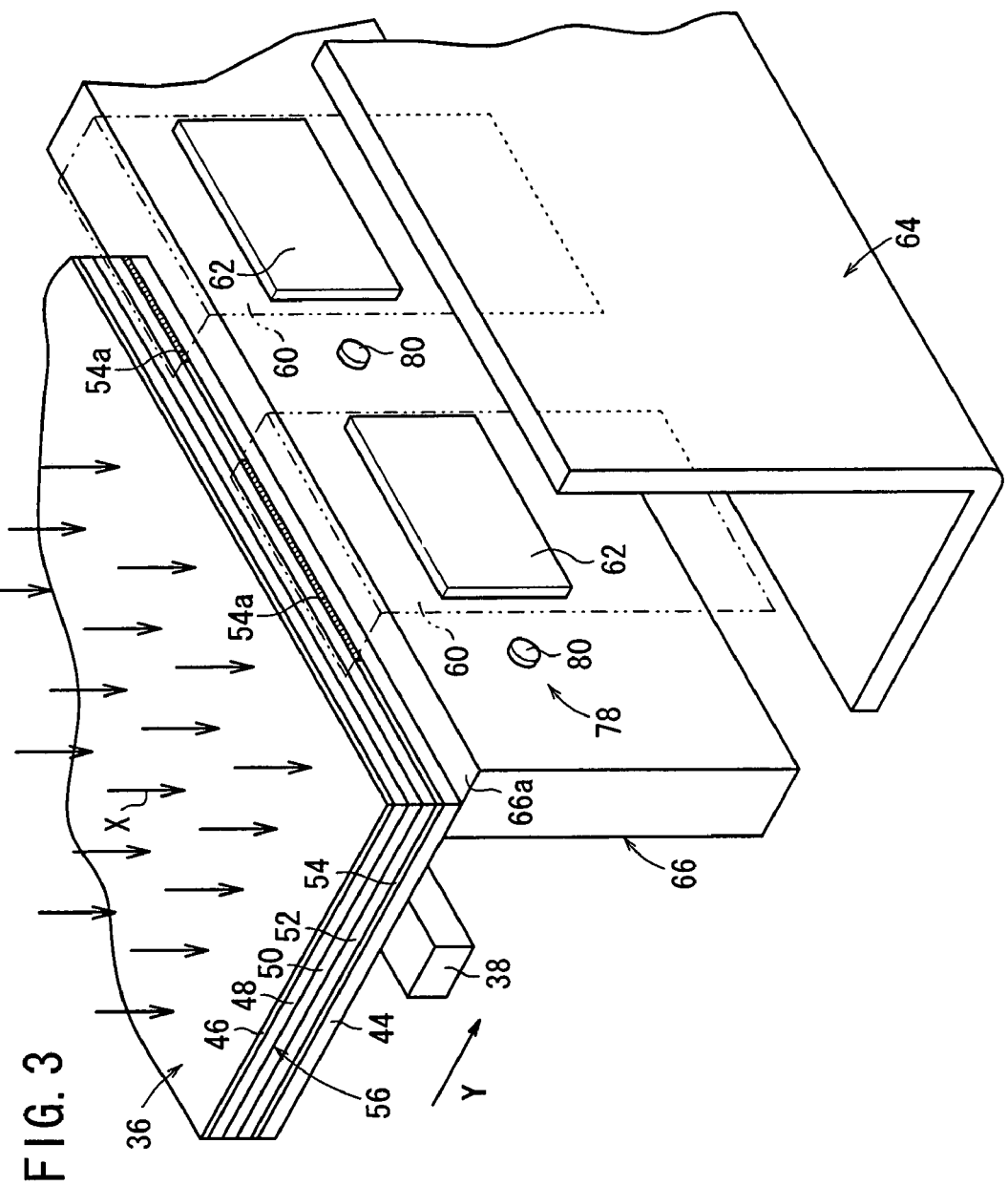
FIG. 3 is a fragmentary exploded perspective view of a solid-state detector and temperature adjustment members in the image capturing base.

As shown in FIG. 3, the solid-state detector 36 comprises a laminated assembly disposed on a glass substrate 44 and made up of a first electrically conductive layer 46 for passing the radiation X therethrough, a recording photoconductive layer 48 for generating electric charges upon exposure to the radiation X, a charge transport layer 50 which acts substantially as an electric insulator with respect to electric charges having latent image polarity developed in the first electrically conductive layer 46 and which acts substantially as an electric conductor with respect to electric charges having charge transport polarity which are of a polarity opposite to the electric charges having the latent image polarity, a reading photoconductive layer 52 for generating electric charges upon exposure to the reading light to be electrically conductive, and a second electrically conductive layer 54 which is permeable to the radiation X. An electric energy storage region 56 is provided in the interface between the recording photoconductive layer 48 and the charge transport layer 50.

Each of the first electrically conductive layer 46 and the second electrically conductive layer 54 provides an electrode. The electrode provided by the first electrically conductive layer 46 comprises a two-dimensional flat electrode. The electrode provided by the second electrically conductive layer 54 comprises a plurality of linear electrodes 54a spaced at a predetermined pixel pitch for detecting the radiation image information to be recorded as an image signal. The linear electrodes 54a are arranged in an array along a main scanning direction, and extend in an auxiliary scanning direction, which is the same as the direction indicated by the arrow Y, perpendicular to the main scanning direction.

The reading light source 38 has, for example, a line light source comprising a linear array of LED chips and an optical system for applying a line of reading light emitted from the line light source to the solid-state detector 36. The linear array of LED chips extends perpendicularly to the direction in which the linear electrodes 54a of the second electrically conductive layer 54 of the solid-state detector 36 extend. The line light source moves along the direction in which the linear electrodes 54a extend to expose and scan the entire surface of the solid-state detector 36.

The erasing light source 42 should preferably comprise a light source which can emit and quench light in a short period of time and which has very short persistence. For example, the erasing light source 42 may comprise a plurality of external-electrode rare-gas fluorescent lamps extending perpendicularly to the direction of the array of LET chips of the reading light source 38 and arranged in an array along the direction of the array of LET chips of the reading light source 38 (see FIG. 2).

As shown in FIG. 3, flexible boards (signal lines) 60 are connected to the respective linear electrodes 54a of the second electrically conductive layer 54 of the solid-state detector 36. Amplifiers 62 are mounted on the respective flexible boards 60 near the linear electrodes 54a. The flexible boards 60 are electrically connected to various boards through an A/D converter, to be described later.

Figure 4:
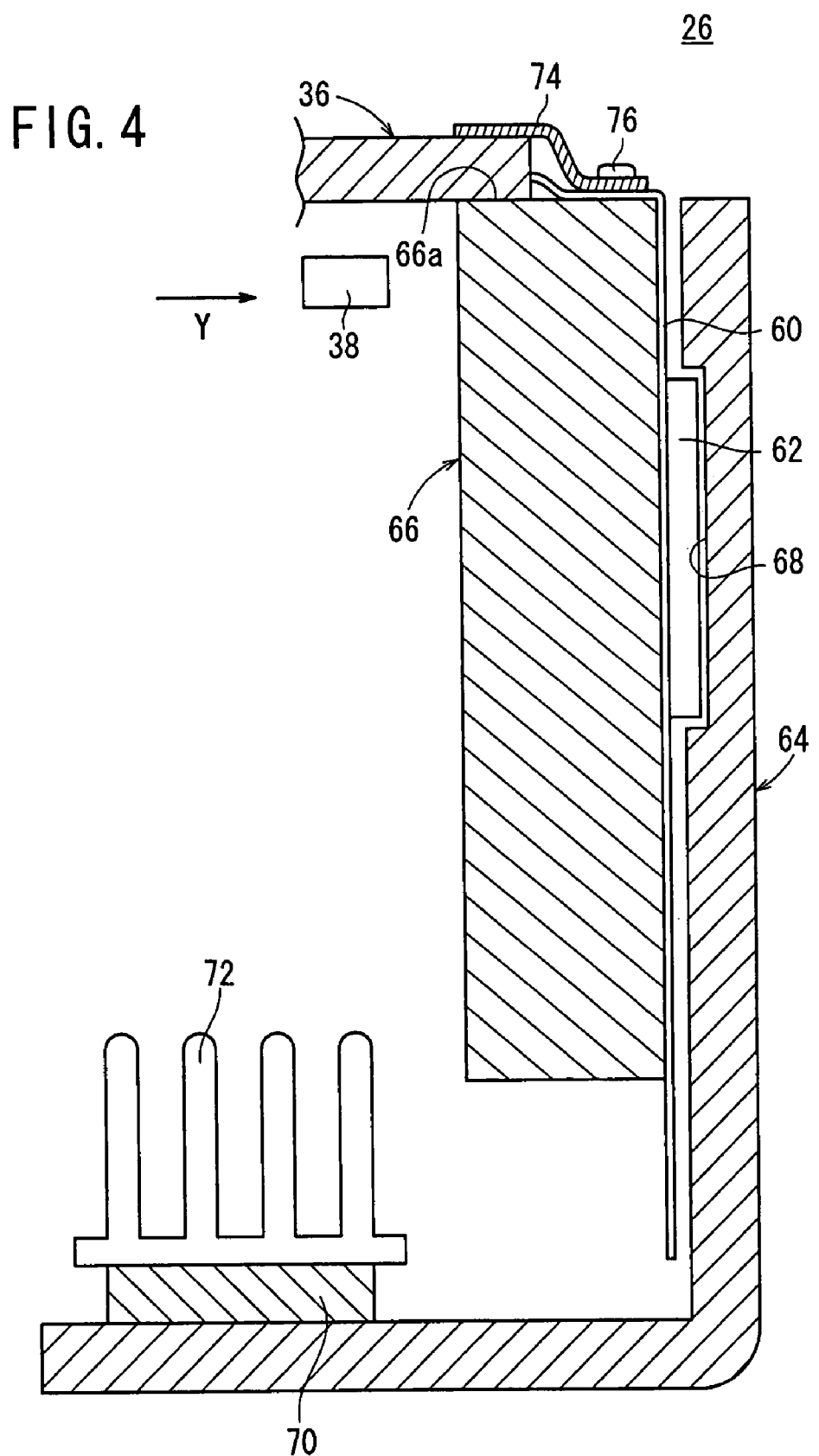
FIG. 4 is a fragmentary side elevational view of the solid-state detector and the temperature adjustment members.

As shown in FIGS. 3 and 4, a first temperature adjustment member 64 is disposed near one of the surfaces of the amplifiers 62 and the flexible boards 60, and a second temperature adjustment member 66 is disposed near the other surface of the flexible boards 60. The first temperature adjustment member 64 and the second temperature adjustment member 66 are secured together by bolts, not shown, for example.

The first temperature adjustment member 64 is made of a metal having a high thermal conductivity and has a substantially L-shaped cross section. The first temperature adjustment member 64 has a recess 68 defined in a surface thereof facing the amplifiers 62. The amplifiers 62 are partly disposed in the recess 68. A temperature adjusting means such as a Peltier device 70, for example, is mounted on a lower horizontal ledge of the first temperature adjustment member 64. A heat sink 72 is mounted on the Peltier device 70.

The Peltier device 70 may be dispensed with, and the heat sink 72 may be mounted directly on the first temperature adjustment member 64. Further alternatively, a heat transfer means such as a heat pipe or the like may be connected to the first temperature adjustment member 64.

The second temperature adjustment member 66 is made of a metal having a high thermal conductivity. The second temperature adjustment member 66 has an upper surface (holder) 66a for directly holding an end of the solid-state detector 36 thereon. An end of an attachment 74 is placed on the upper surface 66a of the second temperature adjustment member 66. The other end of the attachment 74 is placed on an upper surface of the solid-state detector 36. The attachment 74 is fastened to the upper surface 66a of the second temperature adjustment member 66 by bolts 76 (see FIG. 4).

Figure 5:
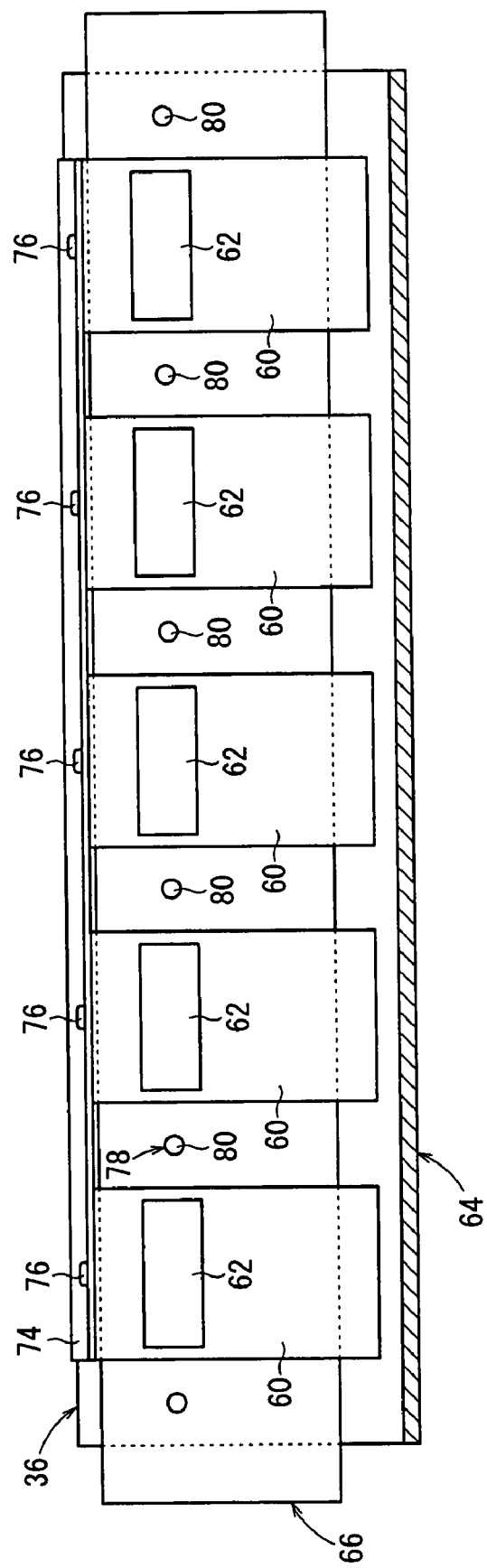
FIG. 5 is a front elevational view of the solid-state detector and the temperature adjustment members.

As shown in FIGS. 3 and 5, a temperature detector 78 for detecting temperatures of the amplifiers 62 is disposed on the second temperature adjustment member 66. The temperature detector 78 comprises a plurality of thermistors (temperature detecting means) 80, adjacent two of which are positioned on each side of each of the amplifiers 62. If there are n of amplifiers 62, then (n+1) of thermistors 80 are disposed on the second temperature adjustment member 66 (see FIG. 5).

Figure 6:
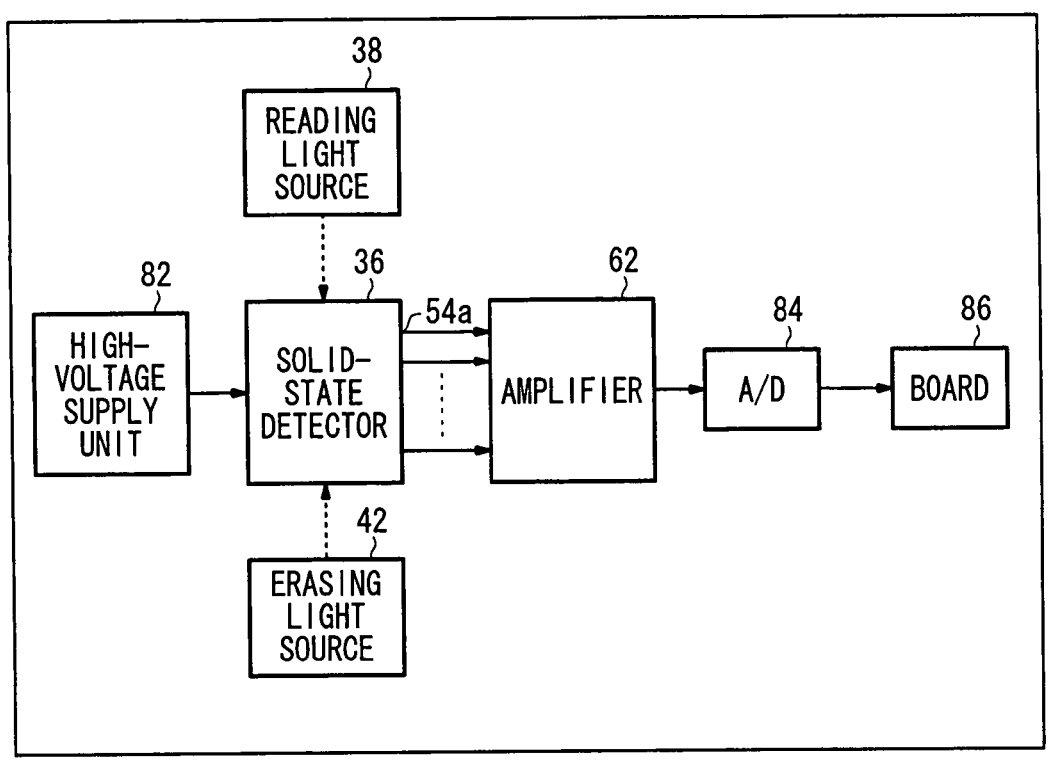
FIG. 6 is a block diagram of a control circuit of the mammographic apparatus.

FIG. 6 shows in block form a control circuit of the mammographic apparatus 10.

As shown in FIG. 6, the control circuit comprises the solid-state detector 36, a high-voltage supply unit 82 for supplying a high voltage to the solid-state detector 36, the amplifiers 62 for amplifying analog electric signals output from the respective linear electrodes 54a of the solid-state detector 36 which is supplied with the high voltage from the high-voltage supply unit 82, an A/D converter 84 for converting the amplified analog electric signals into digital electric signals, and a signal processing board 86 for processing the digital electric signals.

Operation of the mammographic apparatus 10 will be described below.

Using a console and an ID card (not shown), the operator sets ID information and an image capturing method of the subject 22. The ID information represents the name, age, sex, etc. of the subject 22. The image capturing method includes information representing an image capturing region, an image capturing direction, etc. specified by the doctor. The ID information and the image capturing method can be entered by the operator from the console. This information can be displayed for confirmation on the display controller 30 of the mammographic apparatus 10.

Thereafter, the operator places the mammographic apparatus 10 into a certain state according to the specified image capturing method. For example, the breast 34 may be imaged as a cranio-caudal view (CC) taken from above (see FIG. 2), a medio-lateral view (ML) taken from the side of the chest, or a medio-lateral oblique view (MLO) taken from an oblique view. Depending on a selected one of these image capturing views, the operator turns the arm 20 about the swing shaft 18.

Then, the operator places the subject 22 into a specified image capturing state with respect to the mammographic apparatus 10. For example, if a left breast 34 of the subject 22 is to be imaged as a cranio-caudal view (CC), then the operator places the left breast 34 on the image capturing base 26, and thereafter lowers the compression plate 28 to hold the breast 34 between the image capturing base 26 and the compression plate 28, as shown in FIG. 2.

Then, the operator energizes the radiation source housed in the radiation source housing unit 24 to capture radiation image information. Specifically, the radiation X emitted from the radiation source passes through the breast 34 held between the compression plate 28 and the image capturing base 26, and is applied to the solid-state detector 36 housed in the image capturing base 26. Before a radiation image is captured, the entire surface of the solid-state detector 36 is irradiated with the erasing light from the erasing light source 42 to remove unwanted electric charges from the solid-state detector 36.

After the radiation X has passed through the breast 34, the radiation X carries radiation image information of the breast 34. When the radiation X which carries the radiation image information of the breast 34 is applied to the solid-state detector 36 while a high voltage is being applied between the first electrically conductive layer 46 and the second electrically conductive layer 54 by the high-voltage supply unit 82, pairs of positive and negative electric charges are generated in the recording photoconductive layer 48 of the solid-state detector 36, and the negative electric charges are stored in the electric energy storage region 56 that is provided in the interface between the recording photoconductive layer 48 and the charge transport layer 50. The amount of the stored negative electric charges, i.e., the amount of electric charges having latent image polarity, is substantially proportional to the dose of the radiation X that has passed through the breast 34. The positive electric charges generated in the recording photoconductive layer 48 are attracted to the first electrically conductive layer 46 in which they are combined with the negative electric charges supplied from the high-voltage supply unit 82 and are eliminated.

After the radiation image information is captured, the reading light source 38 is moved in the direction indicated by the arrow Y by the scanner 40 while applying the reading light to the solid-state detector 36.

In the solid-state detector 36, pairs of positive and negative electric charges are generated in the reading photoconductive layer 52, and the positive electric charges are attracted to the negative electric charges (latent image polarity electric charges) stored in the electric energy storage region 56 and move in the charge transport layer 50. The positive electric charges are then coupled to the negative electric charges in the electric energy storage region 56 and are eliminated. The negative electric charges generated in the reading photoconductive layer 52 are coupled to the positive electric charges supplied from the high-voltage supply unit 82 to the second electrically conductive layer 54 and are eliminated.

In this manner, the negative electric charges stored in the solid-state detector 36 are eliminated by the charge coupling, and a current is generated in the solid-state detector 36 due to the movement of the electric charges for the charge coupling. Small electric charges generated in the linear electrodes 54a of the second electrically conductive layer 54 are amplified by the amplifiers 62 mounted on the flexible board 60 as analog electric signals. The analog electric signals are sent to the A/D converter 84 and converted thereby into digital electric signals. The digital electric signals are processed by the signal processing board 86 to produce radiation image information of the breast 34.

According to the first embodiment, as shown in FIGS. 3 and 4, the flexible boards 60 connected to the respective linear electrodes 54a of the solid-state detector 36 extend toward the distal end of the image capturing base 26 in the direction indicated by the arrow Y and are sandwiched between the first temperature adjustment member 64 and the second temperature adjustment member 66. Therefore, as shown in FIG. 1, the solid-state detector 36 can be positioned as closely to the subject 22 as possible.

The first temperature adjustment member 64 is disposed near one of the surfaces of the amplifiers 62 and the flexible boards 60, and the second temperature adjustment member 66 is disposed near the other surface of the flexible boards 60. The first temperature adjustment member 64 is effective to adjust the temperature of the amplifiers 62, e.g., to cool the amplifiers 62, and also to prevent heat from being transferred from the one of the surfaces of the flexible boards 60 to the solid-state detector 36. The second temperature adjustment member 66 is effective to prevent heat from being transferred from the other surface of the flexible boards 60 to the solid-state detector 36.

Accordingly, the temperature of the amplifiers 62 is effectively controlled, and heat is prevented from being transferred from the amplifiers 62 to the solid-state detector 36 through the flexible boards 60, with the simple structure. The solid-state detector 36 is thus allowed to produce high-quality radiation image information efficiently.

Furthermore, the distal end of the solid-state detector 36 is directly placed on the upper surface 66a of the second temperature adjustment member 66 and retained on the upper surface 66a by the attachment 74. The image capturing base 26 is not unduly large in size in the direction indicated by the arrow Y, but remains effectively small in size as a whole.

The Peltier device 70, for example, is mounted as a temperature adjusting means on the first temperature adjustment member 64, and the heat sink 72 is mounted on the Peltier device 70. The Peltier device 70 combined with the heat sink 72 improves the temperature adjusting capability of the first temperature adjustment member 64 for reliably adjusting the temperature of the amplifiers 62 to a desired temperature. A heat transfer means such as a heat pipe or the like may be employed instead of the Peltier device 70 to improve the temperature adjusting capability of the first temperature adjustment member 64.

As shown in FIG. 5, the thermistors 80 are mounted on the second temperature adjustment member 66 such that adjacent two of the thermistors 80 are positioned on each side of each of the amplifiers 62. Therefore, the dimension (thickness) of the second temperature adjustment member 66 in the direction indicated by the arrow Y is smaller than if the thermistors 80 are directly mounted on the amplifiers 62, making the image capturing base 26 relatively small in overall size.

If the temperatures measured by the respective thermistors 80 that are positioned on each side of each of the amplifiers 62 are indicated by $\theta_J, \theta_{J+1}$, respectively, then the temperature of the amplifier 62 disposed between the thermistors 80 is indicated by $(\theta_J + \theta_{J+1})/2$. By controlling the Peltier device 70 based on the calculated temperatures of the thermistors 80, the actual temperatures of the amplifiers 62 can be controlled in a desired temperature range, e.g., in a temperature range from 20° C. to 40° C. in terms of temperatures measured at the positions of the thermistors 80.

In the first embodiment, the solid-state detector 36 is employed as a converter. The solid-state detector 36 may comprise a device handling small electric charges such as thin-film transistors (TFTs), highly sensitive CCDs (Charge-Coupled Devices), or the like.

Figure 7:
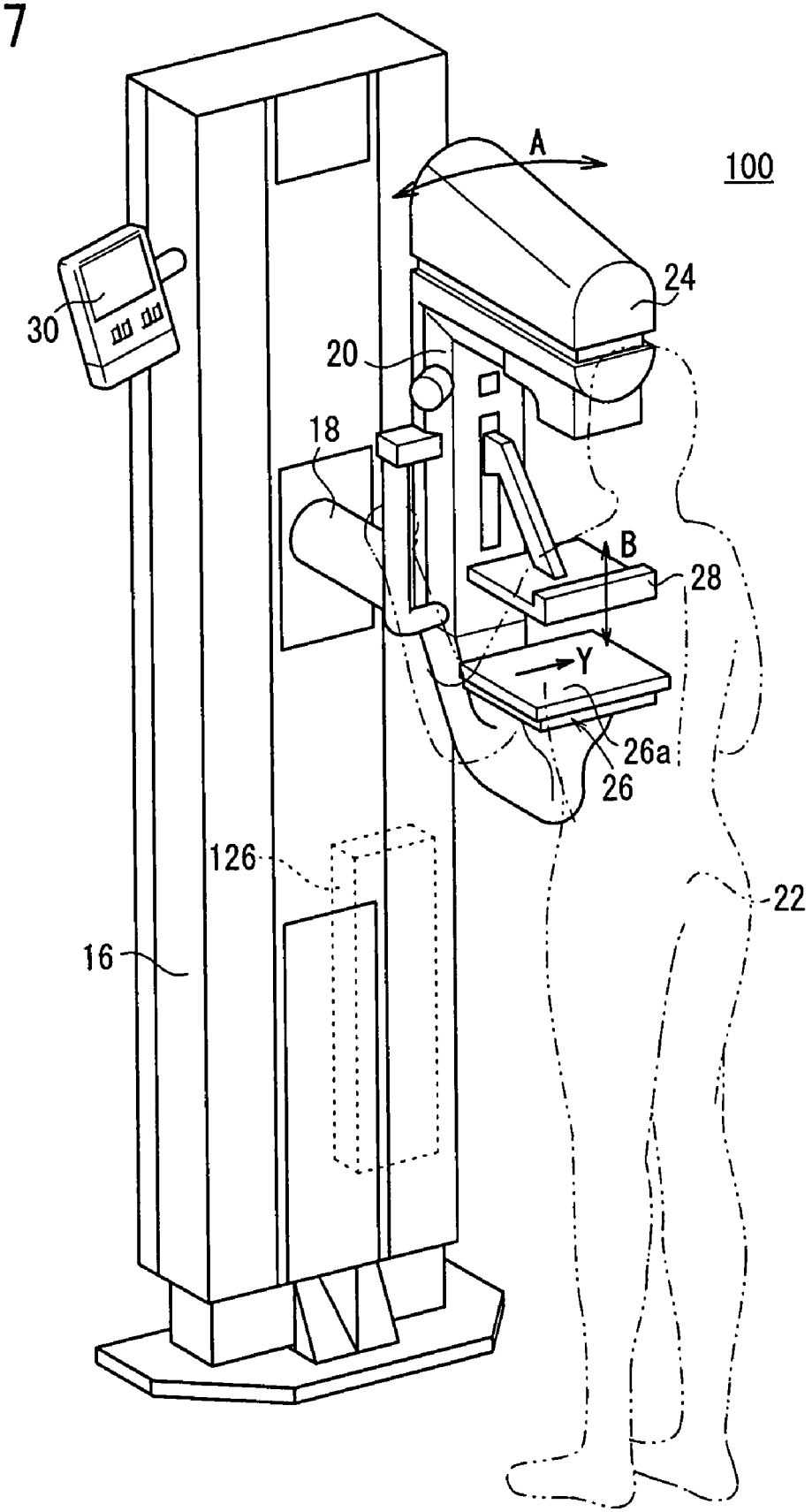
FIG. 7 is a perspective view of a mammographic apparatus according to a second embodiment of the present invention.
Figure 8:
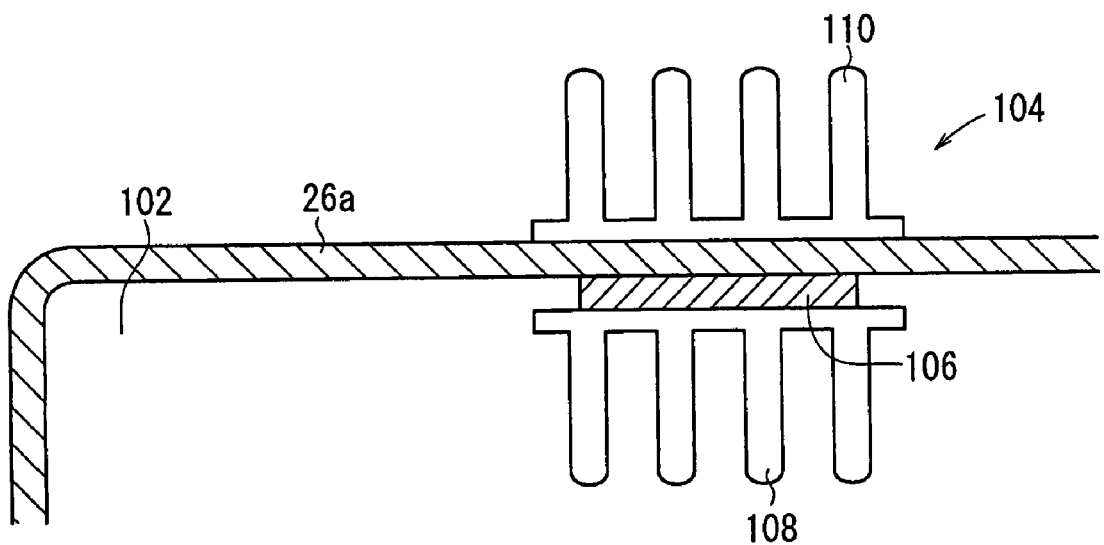
FIG. 8 is a sectional side elevational view of a casing and a heat exchanger of an image capturing base of the mammographic apparatus shown in FIG. 7.
Figure 9:
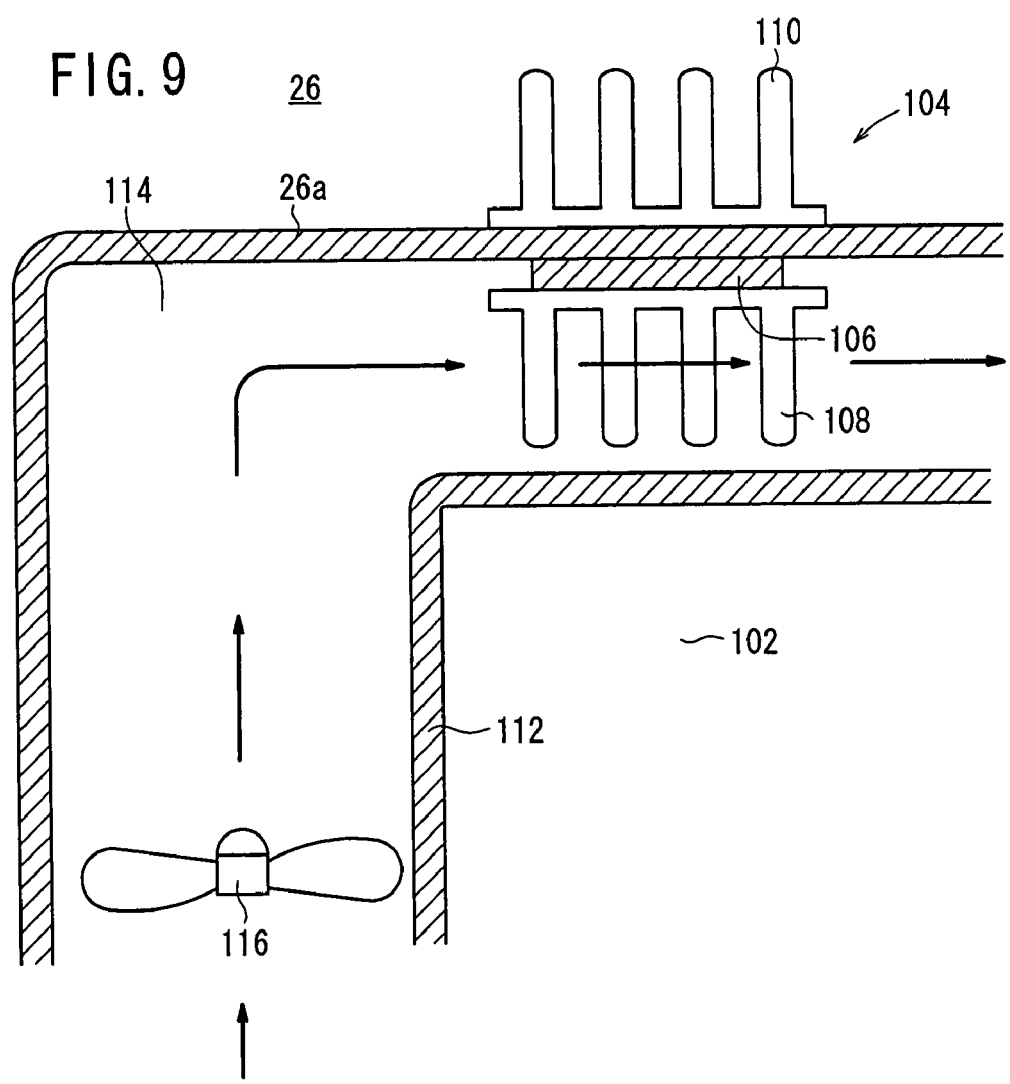
FIG. 9 is a sectional side elevational view showing a circulation passage combined with the casing and the heat exchanger shown in FIG. 8.
Figure 10:
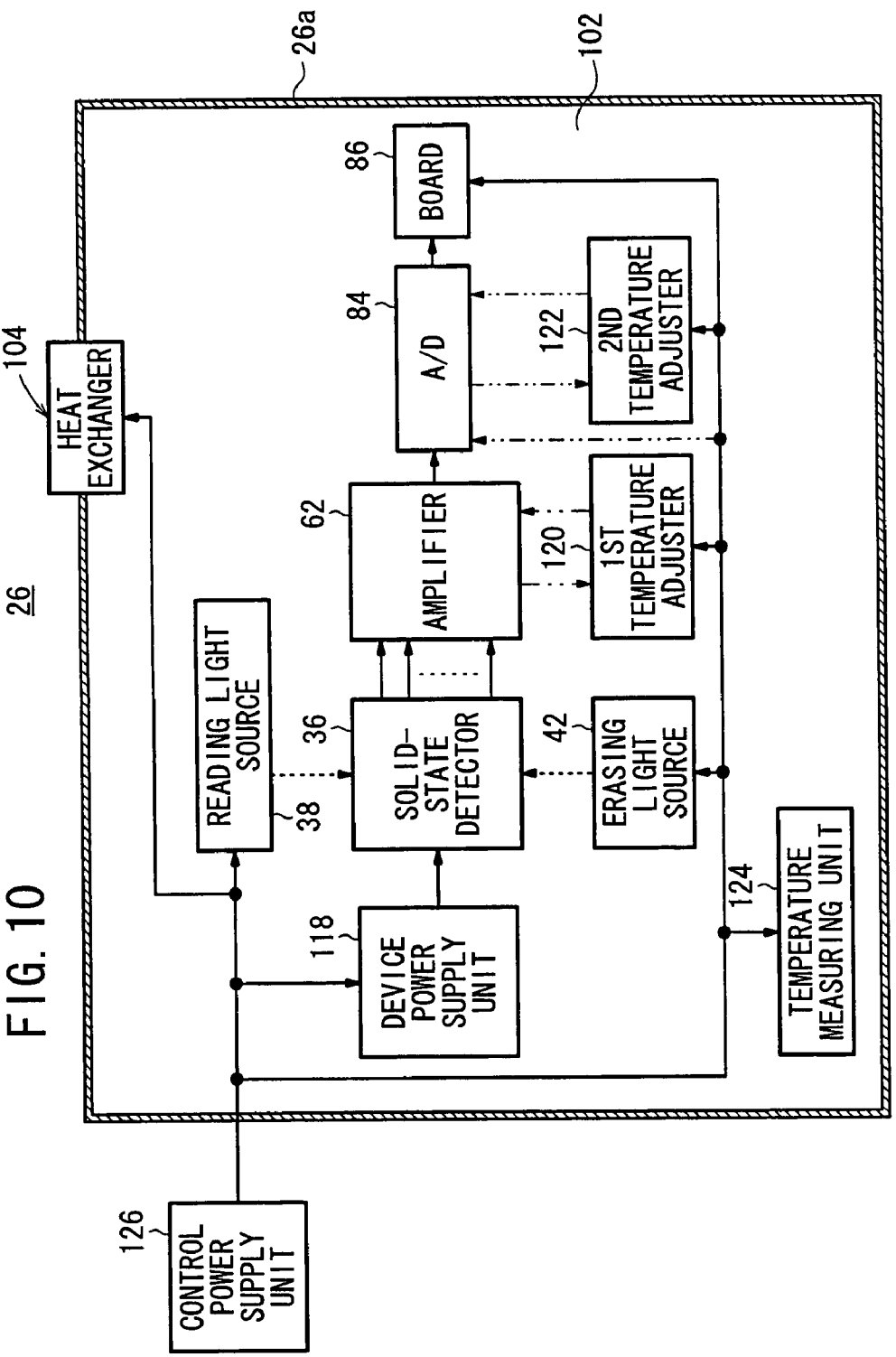
FIG. 10 is a block diagram of a control circuit housed in the casing.

FIG. 7 shows in perspective a mammographic apparatus 100 which is a radiation image information capturing apparatus according to a second embodiment of the present invention. FIGS. 8 through 10 show details of the radiation image information capturing apparatus according to the second embodiment. Those parts of the mammographic apparatus 100 which are identical to those of the mammographic apparatus 10 according to the first embodiment are denoted by identical reference characters, and will not be described in detail below. Similarly, identical parts of mammographic apparatus according to third and fourth embodiments to be described below will not be described in detail below.

As shown in FIG. 8, the casing 26a of the image capturing base 26 has a space 102 defined therein which is essentially closed from outside the casing 26a. The casing 26a supports thereon a heat exchanger 104 for adjusting the temperature of air in the space 102 through a heat exchange with a heat medium outside the casing 26a.

The heat exchanger 104 is disposed remotely from the subject 22, e.g., on a portion of the casing 26a close to the base 16. The heat exchanger 104 comprises a temperature adjusting means, e.g., a Peltier device 106, mounted on an inner wall surface of the casing 26a. A heat sink 108 which mainly serves to absorb heat is positioned in the space 102 and fixedly mounted on the Peltier device 106. Another heat sink 110 which mainly serves to radiate heat is fixedly mounted on an outer wall surface of the casing 26a in alignment with the heat sink 108.

The image capturing base 26 incorporates a structure for circulating air in the space 102 or a structure for producing a forced convective flow of air in the space 102 for allowing the Peltier device 106 to uniformly control the temperature in the space 102 as a whole.

For example, as shown in FIG. 9, a wall plate 112 is disposed in the space 102 to provide a circulatory passage 114 defined between the wall plate 112 and the inner wall surface of the casing 26a. A fan 116 is disposed in the circulatory passage 114. The wall plate 112 comprises a metal plate having a high thermal conductivity. When the fan 116 rotates to generate an air flow in the circulatory passage 114, the air flow is cooled and/or heated by the heat sink 108 under temperature control of the Peltier device 106. The temperature-controlled air exchanges heat with the air in the space 102 while flowing through the circulatory passage 114, thereby adjusting the temperature in the space 102 as a whole.

FIG. 10 shows in block form a control circuit housed in the image capturing base 26 of the mammographic apparatus 100.

As shown in FIG. 10, the control circuit comprises the solid-state detector 36, a device power supply unit 118 for supplying a high power supply voltage to the solid-state detector 36, the amplifiers 62 for amplifying analog electric signals output from the respective linear electrodes of the solid-state detector 36 which is supplied with the high voltage from the device power supply unit 118, the A/D converter 84 for converting the amplified analog electric signals into digital electric signals, the signal processing board 86 for processing the digital electric signals, the heat exchanger 104, a first temperature adjuster (the first and second temperature adjustment members 64, 66) 120, a second temperature adjuster 122 for adjusting the temperature of the A/D converter 84, and a temperature measuring unit (temperature sensor) 124 for detecting the temperature in the space 102. The second temperature adjuster 122 may be of the same arrangement as the first temperature adjuster 120.

The signal processing board 86, the reading light source 38, the erasing light source 42, the heat exchanger 104, the first temperature adjuster 120, the second temperature adjuster 122, and the temperature measuring unit 124 are supplied with a power supply voltage from a control power supply unit 126 disposed outside the image capturing base 26. The control power supply unit 126 is housed in the base 16, for example, as shown in FIG. 7.

According to the second embodiment, as shown in FIG. 10, since the control power supply unit 126 is disposed outside the casing 26a of the image capturing base 26, the casing 26a may be relatively small in size. The casing 26a houses the device power supply unit 118 therein. Therefore, the power transmission path between the device power supply unit 118 and the solid-state detector 36 is short enough not to pick up unwanted external noise.

The essentially closed space 102 is defined in the casing 26a, and the air in the space 102 is adjusted in temperature by the heat exchanger 104. Therefore, the temperature of the air in the space 102 is not affected by the temperature of ambient air unlike the conventional system wherein external air is directly drawn into the casing 26a. It is thus possible to control the temperature of the air in the casing 26a easily and reliably with high accuracy for efficiently obtaining high-quality radiation image information.

According to the second embodiment, as shown in FIGS. 8 and 9, the heat exchanger 104 has the Peltier device 106 disposed on the inner wall surface of the casing 26a. The heat sink 108 is positioned in the space 102 and fixedly mounted on the Peltier device 106, and the heat sink 110 is fixedly mounted on the outer wall surface of the casing 26a.

The heat sink 108 mainly serves to absorb heat, and the heat sink 110 mainly serves to radiate heat. When the heat sink 108 cools the air in the space 102, the heat sink 110 radiates the heat through a heat exchange with the external air. An air blower such as a fan or the like is disposed outside the casing 26a to allow the heat sink 110 to radiate the heat more effectively based on a forced convective flow of the external air.

Similarly, as shown in FIG. 9, a forced convective flow of air is generated in the space 102 to allow the heat sink 108 to absorb the heat quickly from the air in the space 102. Accordingly, the cooling capability of the space 102 is increased.

As shown in FIG. 10, the temperature measuring unit 124 is disposed in the space 102 for detecting the temperature in the space 102. Based on the temperature detected by the temperature measuring unit 124, the Peltier device 106 is energized to control the temperature in the space 102 highly accurately. The first temperature adjuster 120 and the second temperature adjuster 122 are associated respectively with the amplifiers 62 and the A/D converter 84 which generate heat. The amplifiers 62 and the A/D converter 84 can thus be adjusted in temperature individually and effectively.

Figure 11:
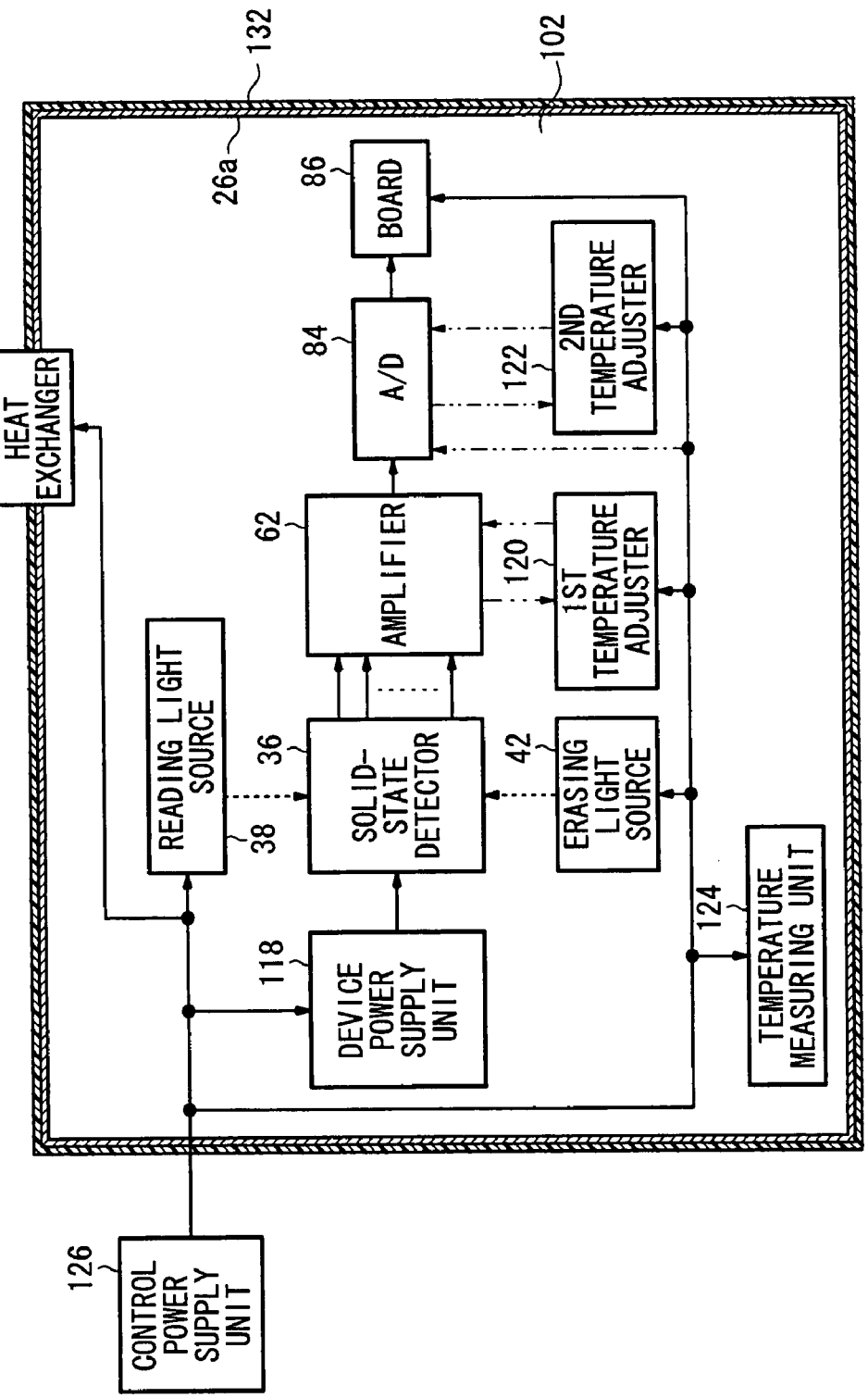
FIG. 11 is a block diagram of a control circuit housed in an image capturing base of a mammographic apparatus according to a third embodiment of the present invention.

FIG. 11 shown in block form a control circuit housed in an image capturing base 130 of a mammographic apparatus according to a third embodiment of the present invention.

As shown in FIG. 11, the entire outer wall surface of the casing 26a is covered with a heat insulating member 132 of resin. The space 102 in the casing 26a is effectively and reliably thermally insulated from the ambient environment by the heat insulating member 132 to permit the temperature of the air in the space 102 to be adjusted with higher accuracy. The heat insulating member 132 may be disposed on the inner wall surface of the casing 26a.

Figure 12:
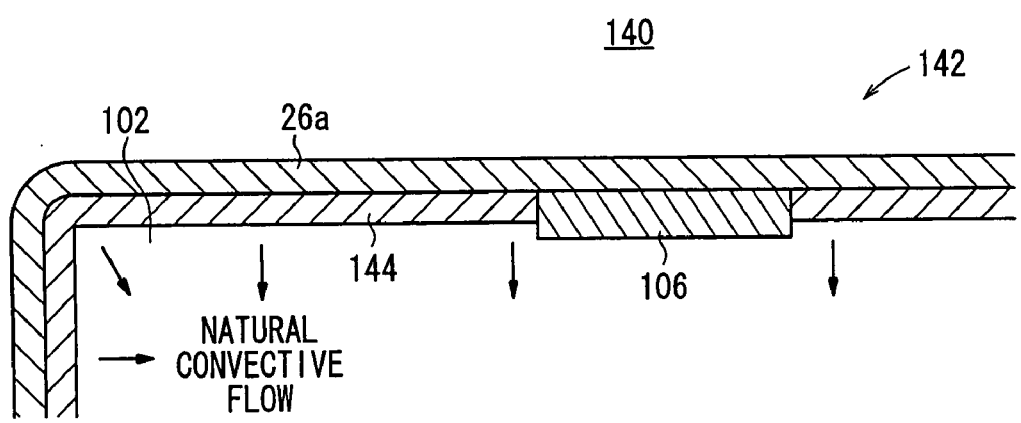
FIG. 12 is a sectional side elevational view of an image capturing base of a mammographic apparatus according to a fourth embodiment of the present invention.
Figure 13:
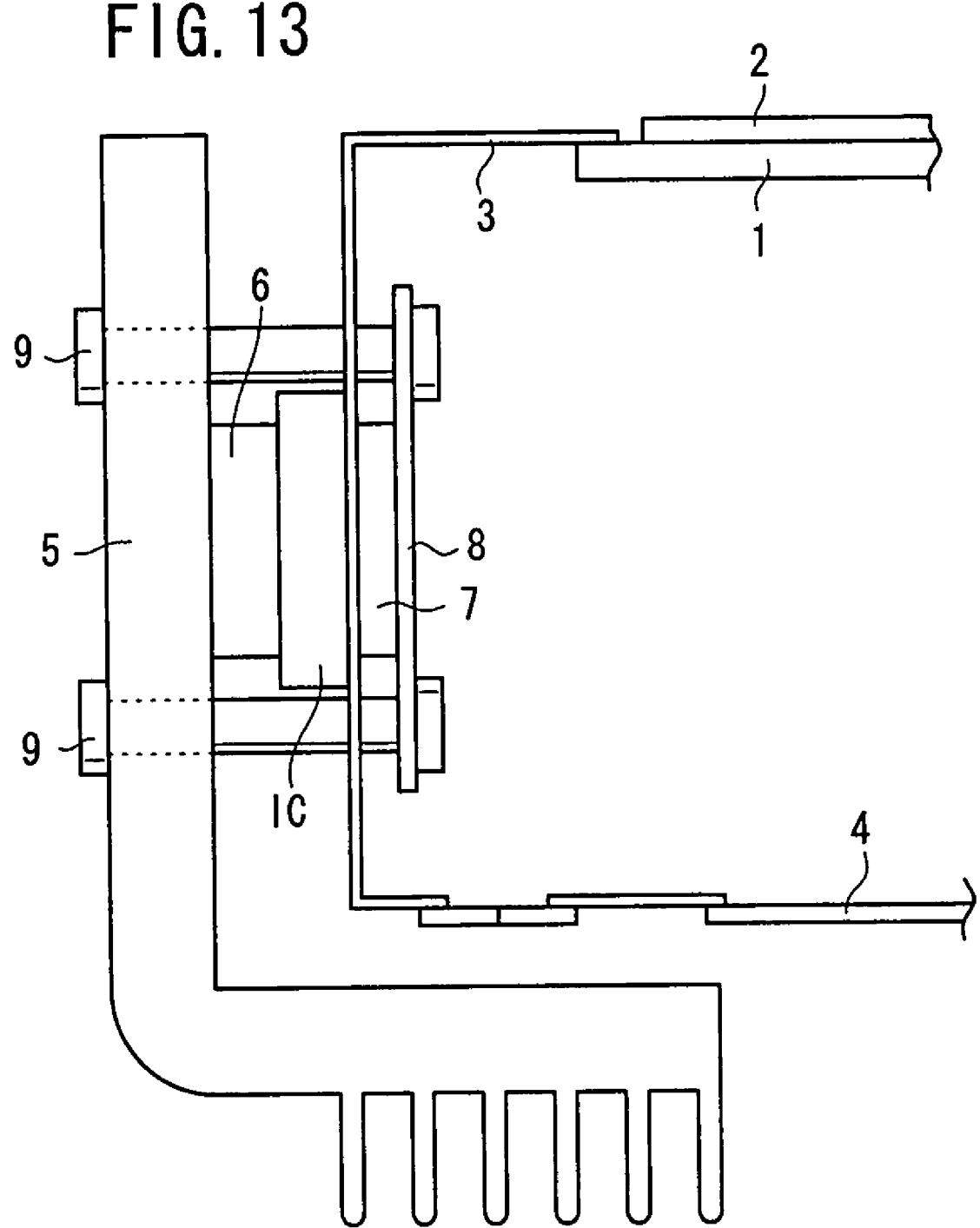
FIG. 13 is a side elevational view of a radiation image capturing apparatus according to the conventional art 1.
Figure 14:
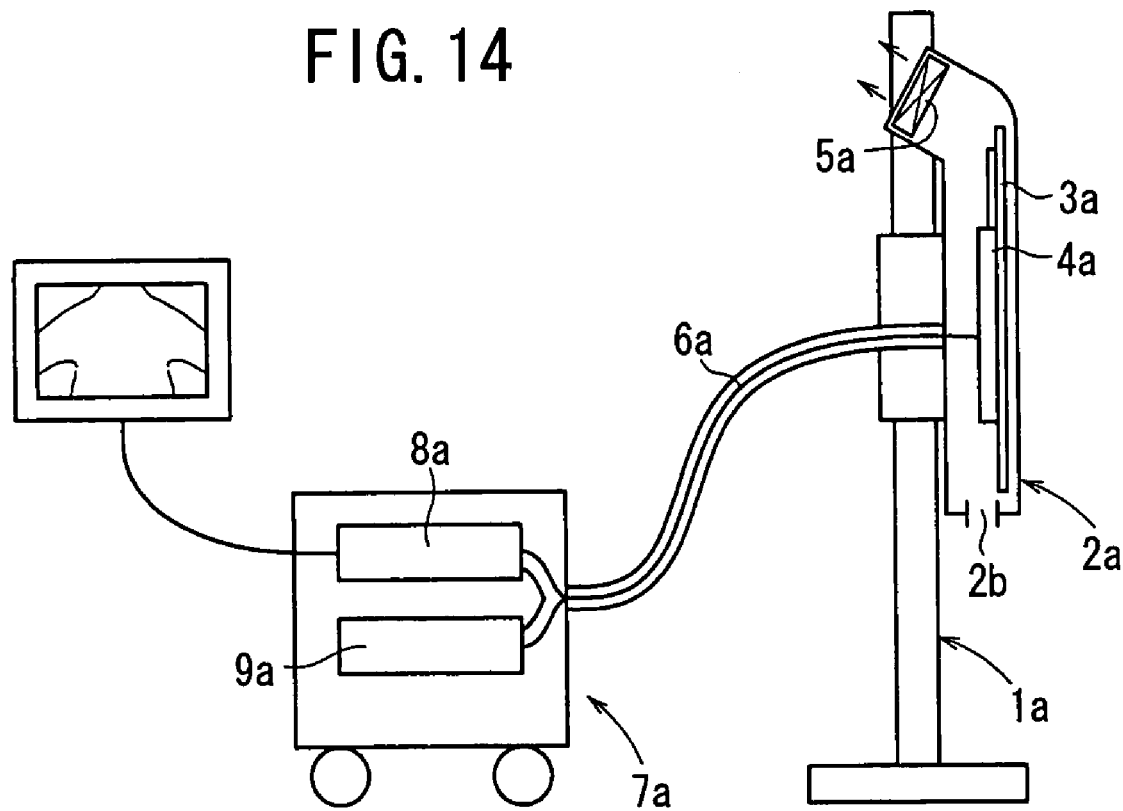
FIG. 14 is a side elevational view of a radiation image capturing apparatus according to the conventional art 3.

FIG. 12 shows in sectional side elevation an image capturing base 140 of a mammographic apparatus according to a fourth embodiment of the present invention.

As shown in FIG. 12, the casing 26a of the image capturing base 140 supports a heat exchanger 142 thereon. The heat exchanger 142 comprises a Peltier device 106 mounted on an inner wall surface of the casing 26a and a coating layer 144 of aluminum, for example, disposed on the inner wall surface of the casing 26a.

According to the fourth embodiment, when the Peltier device 106 is energized for temperature control, a natural convective flow of air is generated in the space 102 through the coating layer 144 to control the temperature of the air in the space 102. Heat is radiated from the Peltier device 106 based on the thermal conductivity of the casing 26a itself. Therefore, the temperature of the air in the space 102 can be controlled highly accurately with a simple and economical arrangement.

In the second through fourth embodiments, as described above, the Peltier device 106 is employed as the temperature adjusting means. However, the temperature adjusting means should not be limited to the Peltier device 106, but may be of any of various other structures. For example, a pipe for circulating a heat medium may be disposed in the space 102 and a radiator may be mounted on the casing 26a, so that a heat exchange may take place between the heat medium and the external air or external cooling water.

Although certain preferred embodiments of the present invention have been shown and described in detail, it should be understood that various changes and modifications may be made therein without departing from the scope of the appended claims.

What is claimed is:

1. A radiation image information capturing apparatus for reading the radiation image information of a subject by converting the radiation image information into an electric signal, comprising:

a converter for converting the radiation image information of the subject into the electric signal;

an amplifier connected to said converter by a signal line comprising a flexible board for amplifying the electric signal produced by said converter;

a first temperature adjustment member disposed near one surface of said amplifier and said signal line;

a second temperature adjustment member disposed near another surface of said signal line;

wherein the first temperature adjustment member is disposed near a first surface of said signal line and the second adjustment member is disposed near a second surface of said signal line, wherein said first surface and said second surface are on opposite sides of said signal line, wherein said converter is horizontally held on an upper surface of the first temperature adjustment member or the second temperature adjustment member; and wherein the flexible board is vertically extended and is disposed between the first temperature adjustment member and the second temperature adjustment member;

a temperature detector for detecting the temperature of said amplifier;

wherein said temperature detector comprises a plurality of thermistors each of which is disposed on each side of said amplifier.

2. A radiation image information capturing apparatus according to claim 1, wherein said first temperature adjustment member or said second temperature adjustment member has a holder for holding said converter.

3. A radiation image information capturing apparatus according to claim 2, wherein said holder comprises a temperature adjustment member upper surface for directly holding an end of said converter.

4. A radiation image information capturing apparatus according to claim 1, wherein said first temperature adjustment member or said second temperature adjustment member comprises a Peltier device.

5. A radiation image information capturing apparatus according to claim 1, wherein said amplifier and said signal line are controlled in a temperature range from 20° C. to 40° C. by said first temperature adjustment member and said second temperature adjustment member.

6. A radiation image information capturing apparatus for reading the radiation image information of a subject by converting the radiation image information into an electric signal, comprising:
a casing housing therein a converter for converting the radiation image information of the subject into the electric signal, an amplifier for amplifying the electric signal produced by said converter, a signal processor for processing the amplified electric signal, and a device power supply unit for supplying a power supply voltage at least to said converter;
a control power supply unit disposed outside said casing;
said casing having a space defined therein which is essentially closed from outside of said casing;
said casing having a first side confronting the subject and second and third sides perpendicular to the first side, wherein the first temperature adjuster and a flexible plate, which has a second temperature adjuster and an amplifier, are disposed on at least one of the second and third sides; and
a heat exchanger supported on said casing for adjusting the temperature of air in said space through heat exchange with a heat medium outside said casing, wherein the control power supply unit supplies power at least to the heat exchanger for adjusting the temperature of the air.

7. A radiation image information capturing apparatus according to claim 6, further comprising
a temperature measuring unit disposed in said casing for detecting the temperature in said space.

8. A radiation image information capturing apparatus according to claim 7, wherein the temperature in said space is controlled in a temperature range from 20° C. to 40° C.

9. A radiation image information capturing apparatus according to claim 6, wherein said heat exchanger comprises a Peltier device.

10. A radiation image information capturing apparatus according to claim 6, wherein said heat exchanger performs a heat exchange between air in said space and external air outside said casing.

11. A radiation image information capturing apparatus according to claim 6, wherein said heat exchanger performs heat exchange between air in said space and said casing.

12. A radiation image information capturing apparatus according to claim 6, further comprising:
a temperature adjuster disposed in said casing for adjusting the temperature of at least said amplifier.

13. A radiation image information capturing apparatus according to claim 6, further comprising:
a heat insulating member disposed on an inner wall surface or an outer wall surface of said casing in enclosing relation to said space.

14. A method of detecting the temperature of an amplifier in a radiation image information capturing apparatus in which a converter for converting the radiation image information of a subject into an electric signal is connected by a signal line to the amplifier for amplifying the electric signal produced by said converter, comprising the steps of:
detecting temperatures respectively with first temperature detecting means disposed on one side of said amplifier and second temperature detecting means disposed on another side of said amplifier; and
setting $(\theta_J + \theta_{J+1})/2$ as the temperature of said amplifier where $\theta_J$ represents the temperature detected by said first temperature detecting means and $\theta_{J+1}$ represents the temperature detected by said second temperature detecting means.

15. A radiation image information capturing apparatus for reading the radiation image information of a subject by converting the radiation image information into an electric signal, comprising:
a casing housing therein a converter for converting the radiation image information of the subject into the electric signal, an amplifier for amplifying the electric signal produced by said converter, a signal processing means for processing the amplified electric signal, and a device power supply means for supplying a power supply voltage at least to said converter;
a heat exchanger supported on said casing for adjusting the temperature of air in stud space through heat exchange with a heat medium outside said casing; and
a control power supply means for supplying power to said heat exchanger and said signal processing means, said control power supply means being disposed outside said casing;
said casing having a space defined therein which is essentially closed from outside of said casing, wherein the control power supply means supplies power at least to the heat exchanger for adjusting the temperature of the air; and
said casing having a first side confronting the subject and second and third sides perpendicular to the first side, wherein the first temperature adjuster and a flexible plate, which as a second temperature adjuster and an amplifier, are disposed on at least one of the second and third sides.

16. The radiation information capturing apparatus according to claim 15, further comprising:
a temperature adjuster disposed in said casing for adjusting the temperature of at least said amplifier and with power supplied by the control power supply means.

* * * * *